United States Patent [19]

Bair

[11] Patent Number: 4,719,236

[45] Date of Patent: *Jan. 12, 1988

[54] PERYLENE DERIVATIVES

[75] Inventor: Kenneth W. Bair, Chapel Hill, N.C.

[73] Assignee: Burroughs Wellcome Co., Research Triangle Park, N.C.

[*] Notice: The portion of the term of this patent subsequent to Jul. 23, 2002 has been disclaimed.

[21] Appl. No.: 661,803

[22] Filed: Oct. 17, 1984

Related U.S. Application Data

[63] Continuation-in-part of Ser. No. 499,813, Jun. 1, 1983, Pat. No. 4,530,800.

Foreign Application Priority Data

[30]

May 16, 1984 [GB] United Kingdom ............... 84105584

[51] Int. Cl.[4] ..................... C07C 67/02; C07C 87/455
[52] U.S. Cl. ................. 514/577; 260/501.12; 260/501.19; 260/501.21; 260/514.2; 514/908; 558/411; 558/422; 564/426; 568/30; 568/32; 568/34; 568/44; 568/49; 568/55; 568/58; 568/585; 568/705; 568/808
[58] Field of Search ........... 260/501.12, 59.19, 501.21, 260/514 J, 465 D; 514/908, 577; 560/252; 564/426; 558/411, 422; 568/30, 32, 39, 44, 49, 55, 58, 585, 705, 808

[56] References Cited

U.S. PATENT DOCUMENTS

| | | | |
|---|---|---|---|
| 3,052,722 | 9/1962 | Ashley | 260/501.19 |
| 4,034,040 | 7/1977 | Cronin et al. | 260/501.19 |
| 4,511,582 | 4/1985 | Bair | 514/654 |
| 4,530,800 | 7/1985 | Bair | 260/501.21 |
| 4,532,344 | 7/1985 | Bair | 560/252 |
| 4,551,282 | 11/1985 | Bair | 260/501.18 |

FOREIGN PATENT DOCUMENTS 0125702 1/1984 European Pat. Off. ........ 260/501.21

Primary Examiner—Glennon H. Hollrah
Assistant Examiner—Raymond Covington

Attorney, Agent, or Firm—Donald Brown

[57] ABSTRACT

The present invention relates to compounds of formula (I)

$$ArCH_2R^1 \qquad (I)$$

or a monomethyl or a monoethyl ether thereof (the compound of formula (I) including these ethers may contain no more than 30 carbon atoms in total); ethers, esters thereof; acid additon salts thereof; wherein Ar is a perylene or substituted perylene ring system; $R^1$ contains not more than eight carbon carbon atoms and is a group

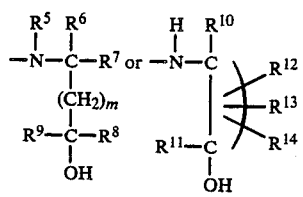

wherein
m is 0 or 1;
$R^5$ is hydrogen;
$R^6$ and $R^7$ are the same or different and each is hydrogen or $C_{1-3}$ alkyl optionally substituted by hydroxy;
$R^8$ and $R^9$ are the same or different and each is hydrogen or $C_{1-3}$ alkyl;

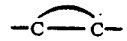

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl; $R^{14}$ is hydrogen, methyl, hydroxy, or hydroxymethyl.

11 Claims, No Drawings

PERYLENE DERIVATIVES

This application is a continuation-in-part of application Ser. No. 499,813, filed June 1, 1983, now U.S. Pat. No. 4,530,800.

The present invention relates to polycyclic aromatic alkanol derivatives which have been found to have biocidal activity. More specifically the invention concerns aminoalkanol derivatives containing a polycarbocyclic aromatic ring system, methods for the synthesis thereof, pharmaceutical formulations thereof, novel intermediates therefor, pharmaceutical formulations thereof and the use thereof as biocidal agents, particularly antitumor agents.

Accordingly, in a first aspect, the present invention provides a compound of the formula (I):

(I)

or a monomethyl or monoethyl ether thereof the (compound of formula (I) including these ethers may contain no more than 30 carbon atoms in total); ethers, esters thereof; acid addition salts thereof;

wherein Ar is a perylene ring optionally substituted by one or two substituents (the substituents will contain not more than four carbon atoms in total when taken together being the the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the perylene ring is optionally substituted by a group $NR^3R^4$ containing not more than 5 carbon atoms wherein $R^3$ and $R^4$ are the same or different and each is a $C_{1-3}$ alkyl group or $NR^3R^4$ forms a five-or six-membered heterocyclic ring optionally containing one or two additional heteroatoms);

$R^1$ contains not more than eight carbon atoms and is a group

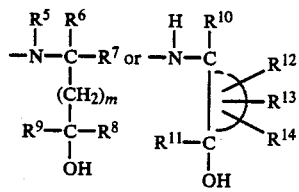

wherein
m is 0 or 1;
$R^5$ is hydrogen;
$R^6$ and $R^7$ are the same or different and each is hydrogen or $C_{1-3}$ alkyl optionally substituted by hydroxy;
$R^8$ and $R^9$ are the same or different and each is hydrogen or $C_{1-3}$ alkyl;

is a five-or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen, methyl, hydroxy, or hydroxymethyl.

Suitably $ArCH_2R^1$ or a monomethyl or monethyl ether thereof contains not more than 28 carbon atoms in total.

Ar is suitably 3-perylenyl,

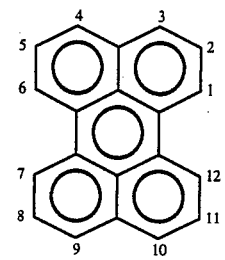

suitably m is 0, suitably $R^1$ is

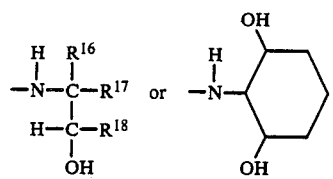

wherein
$R^{16}$ is $CH_2OH$, $CH(CH_3)OH$ or $CH_2CH_2OH$,
$R^{17}$ is hydrogen, $C_{1-3}$ alkyl or $CH_2OH$;
$R^{18}$ is hydrogen or methyl.

Preferably $R^{16}$ is $CH_2OH$ or $CH(CH_3)OH$; $R^{17}$ is hydrogen, methyl, ethyl or $CH_2OH$.

Preferably $R^1$ is a diol of the structure

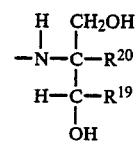

wherein $R^{19}$ is hydrogen or methyl and $R^{20}$ is hydrogen, methyl or ethyl, preferably methyl.

Acid addition salts included within the scope of the present invention are those of compound of formula (I) and ethers and esters thereof.

Esters and nonpharmaceutically useful acid addition salts of the compounds of the formula (I) are useful intermediates in the preparation and purification of compounds of the formula (I) and pharmaceutically useful acid addition salts thereof, and are therefore within the scope of the present invention. Thus, acid addition salts of the the compounds of the formula (I) useful in the present invention include but are not limited to those derived from inorganic acids, such as hydrochloric hydrobromic, sulfuric and phosphoric acids, and organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, naphthalene-2-sulfonic, and ascorbic acids, and amino acids such as glycine.

Acid addition salts particularly useful as biocidal agents are those that are pharmacologically and pharmaceutically acceptable. Thus, preferred salts include but are not limited to those derived from hydrochloric, methanesulfonic, ethanesulfonic, lactic, citric and isethionic acids.

The preferred pharmacologically and pharmaceutically acceptable acid addition salts are those that are soluble in solvents suitable for parenteral administration, for example, hydrochlorides, methanesulfonates and isethionates.

Esters of compounds of formula (I) are derived from acids known to those skilled in the art to be suitable for ester formation, and are conveniently those derived from $C_{1-6}$ alkanoic acids or alkanoic acid derivatives, for example acetic acid, propionic acid, n-butyric acid and iso-butyric acid. The esters may be formed from all or only some of the hydroxy groups contained in the compounds of formula (I). Specific compounds within the scope of formula (I) include;

2-Methyl-2-((3-perylenylmethyl)amino)-1,3-propanediol, 2-((3-Perylenylmethyl)amino)-3-methoxy-2-methyl-1-propanol, (+−)(2R*,3S*)-2-((3-Perylenylmethyl)amino)-2-methyl-1,3-butanediol, 2-((3-Perylenylmethyl)amino)-2-ethoxymethyl-1,3-propanediol, 2-Isopropyl-2-((3-perylenylmethyl)amino)-1,3-propanediol, 2-Methyl-2-((3-perylenylmethyl)amino)-1,4-butanediol and ($1\alpha,2\beta,3\alpha$)-2-((3-Perylenylmethyl)amino)-1,3-cyclohexanediol;

ethers, esters thereof; acid addition salts thereof.

Of these specific examples of compounds of formula (I), the most preferred compound is 2-methyl-2-((3-perylenylmethyl)amino)-1,3-propanediol; ethers, esters thereof; acid addition salts thereof.

The compounds of formula (I) and their ethers, esters, and salts thereof may be prepared by any method known in the art for the preparation of compounds of analogous structure. Thus, the compounds of formula (I) may, for example, be prepared by any of the methods defined below.

1. The reduction of a compound of formula (II)

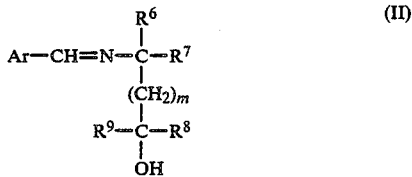

Wherein $R^1$-$R^4$ are as hereinbefore defined or an appropriately protected derivative thereof followed by deprotection where appropriate.

The conditions and reagents for such a reaction are well known to those skilled in the art, and any such conditions/reagents may be employed. The conversion of (II) or suitably protected derivatives thereof may be carried out by a reducing agent followed by deprotection if necessary. The reduction conveniently carried out by a metal hydride such as lithium aluminum hydride, sodium borohydride, sodium cyanoborohydride, or by catalytic hydrogenation, conveniently by hydrogen in the presence of a metal catalyst such as palladium or platinum, or equivalent reagent as outlined by J. March, *Advanced Organic Chemistry*, 2nd ed., pages 819–820, McGraw Hill, New York, 1977. The reduction is suitably carried out with the compound of formula (II) in solution in an inert solvent or mixture of solvents compatible with the reducing agent, at a non-extreme temperature, for example, between 0° and 80° C., conveniently at room temperature.

In the case of lithium aluminum hydride and like reagents, suitable solvents include ethers (for example tetrahydrofuran, diethyl ether and 1,2-dimethoxyethane) optionally in the presence of a hydrocarbon cosolvent (for example toluene, benzene or hexane).

In the case of sodium borohydride and like reagents, suitable solvents include alcohols (for example ethanol, methanol or isopropanol) optionally in the presence of a hydrocarbon cosolvent (for example toluene, benzene or hexane) or an ether cosolvent (for example diethylether or tetrahydrofuran).

In the case of sodium cyanoborohydride and like reagents, suitable solvents include those described for sodium borohydride and in the presence of an acid conveniently glacial acetic acid ethanolic hydrochloric acid as outlined in, for example, R. Hutchins et al., *Organic Preparations and Procedures International* 11, 201 (1979).

In the case of catalytic hydrogenation, suitable solvents include alcohols (for example methanol and ethanol) optionally in the presence of a hydrocarbon cosolvent (for example toluene or benzene) or ether cosolvent (for example diethyl ether or tetrahydrofuran) optionally in the presence of an acid (for example glacial acetic acid or ethanolic hydrochloric acid) or in glacial acetic acid.

Protected derivatives of compounds of formula (II) are conveniently used when lithium aluminum hydride is employed as the reducing agent. Convenient protecting groups are compatible with the reducing agent utilized and are readily removed under nondestructive conditions, for example benzyl, tetrahydropyranyl and isopropylidene ethers.

It is often convenient not to isolate the compound of the formula (II) but to react a compound of the formula (III) with a compound of the formula (IV):

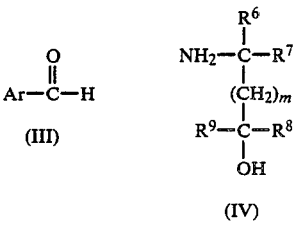

wherein Ar and $R^1$-$R^4$ are as defined in (I), and reduce the compound of the formula (II) so formed in situ. The reaction of the compounds of the formulae (III) and (IV) is again suitably carried out using conditions and reagents which are well known to those skilled in the art, for example in the presence of an acid, such as a sulfonic acid, i.e. p-toluenesulfonic acid, in an appropriate inert solvent, such as an aromatic hydrocarbon, for suitably toluene, with azeotropic removal of water followed by treatment with the reducing agent in an appropriate solvent, suitably ethanol or methanol. Alternatively, (II) formed under equilibrium conditions in appropriate solvents can be reduced in situ with an appropriate reducing agent, suitably sodium cycanoborohydride.

The compound of formula (III) may be in the form of a protected aldehyde, for example an acetal, which liberates the aldehyde function under the reaction conditions.

In turn, a compound of formula (III) can be synthesized by reacting the appropriate polycyclic aromatic hydrocarbon with a formylating agent such as that generated by the reaction between SnCl$_4$ and Cl$_2$CHOCH$_3$ or equivalent reagents, for example, according to the method of A. Reiche et al., *Chem. Ber.* 93, 88 (1960), or with other standard formylating reagents/procedures known to the art, for example, the Gatterman-Koch reaction (CO/HCl/AlCl$_3$/CuCl), the Gatterman reaction (HCN/HCl/ZnCl$_2$), and the Vilsmeier reaction (POCl$_3$/PhN(Me)CHO or POCl$_3$·/Me$_2$NCHO) (J. March, vide supra pages 494–497).

The compounds of the formula (III) may also be prepared from an appropriate polycyclic aromatic hydrocarbon substituted by a suitable functional group such as CH$_2$OH, CHBr$_2$, CH$_3$, COCH$_3$, COOH, or CN, and converting this functional group to an aldehyde group by methods well known to those skilled in the art.

Where the polycyclic aromatic ring bears substituents, the compound of formula (III) may be prepared by a variety of methods known in the art of organic chemistry depending on the nature of the substituent on the polycyclic ring. For example, if the substituent(s) is a halogen, the starting materials may be prepared by direct treatment of the polycyclic aromatic hydrocarbon with a halogenating agent (e.g. Cl$_2$, Br$_2$, or SO$_2$Cl$_2$) or indirectly by such routes as the Sandmeyer reaction (H. H. Hodgson, *Chem. Rev.* 40, 251 (1947). If the substituent(s) is alkyl, the polycyclic aromatic hydrocarbon may be reacted with the appropriate reagents under Friedel-Crafts reaction conditions (G. A. Olah, *Friedel Crafts and Related Reactions*, Vols. 1–3, Interscience, New York, NY, 1963-1965).

The compounds of the formula (IV) also may be prepared by methods known in the art, for example, by the reaction of compound NO$_2$CH$_2$R$^2$ with an appropriate aldehyde, conveniently acetaldehyde or formaldehyde (as in B. M. Vanderbilt and H. B. Hass, *Ind. Eng. Chem.* 32, 34 (1940)) followed by reduction (as outlined in J. March, vide supra, pages 1125–1126), conveniently by hydrogen and a metal catalyst (for example, a platinum containing catalyst) in an appropriate solvent, conveniently glacial acetic acid.

2. The reduction of a compound of the formula (V)

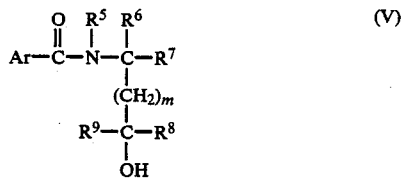

(V)

wherein Ar and R$^1$–R$^4$ are as hereinbefore defined and the hydroxy groups are optionally protected, followed by deprotection of the hydroxy groups where appropriate. The reduction may be carried out by standard reducing agents known for carrying out this type of reduction (as outlined in J. March, vide supra, page 1122), for example, a hydride reagent such as lithium aluminium hydride in an inert solvent, such as an ether, i.e. tetrahydrofuran, at a non-extreme temperature, for example, at between 0° and 100° C. and conveniently at the reflux temperature of the ether.

The compound of the formula (V) may be formed by the reaction of the appropriate acid (ArCOOH) or a suitable reactive acid derivative thereof as outlined in J. March, vide supra, pages 382–390) for example, an acid halide in an inert solvent, with an amine of the formula (IV) in which the hydroxy groups are optionally protected, for example, when the compound of the formula (IV) is a diol, by an isopropylidene group. The compound of the formula (V) so formed is suitably reduced in situ and deprotected if necessary to give a compound of formula (I). The compounds of the formula Ar-COOH can be prepared by methods well known to those skilled in the art.

3. The reaction of a compound ArCH$_{d2}$L (wherein Ar is as hereinbefore defined and L is a leaving group), with a compound of the formula (IV) as hereinbefore defined. Suitable leaving groups are those defined by J. March, vide supra pages 325–331, and include halogens such as chlorine or bromine and sulfonic acid derivatives such as p-toluenesulfonate. The reaction is suitably carried out in an appropriate solvent, such as a dipolar aprotic solvent or alcohol at a non-extreme temperature, for example 50°–100°. The compounds of the formula ArCH$_2$L can be prepared by methods well known to those skilled in the art.

There is therefore provided, as a further aspect of the invention, a method for the preparation of a compound of formula (I) comprising any method known for the preparation of analogous compounds, in particular those methods defined in (1) to (3) hereinabove.

The compounds of this invention have biocidal activity, e.g. are toxic to certain living cells which are detrimental to mammals, for example pathogenic organisms and tumor cells.

This toxicity to pathogenic organisms has been demonstrated by activity against viruses (e.g. *Herpes simplex* 1/vero), fungi (e.g. *Candida albicans*), protozoa (e.g. *Eimeria tenella* and *Trichomonas vaginalis*), bacteria (e.g. *Mycoplasma smegmatis* and *Streptococcus pyogenes*), and helminths (e.g. *Nippostrongylus brasiliensis* and *Brugia pahangi*). The antitumor activity of compounds of formula (I) has been demonstrated in a number of recognized screens and primarily by activity against ascitic P388/O leukemia.

Preferred compounds of the formula (I) are those which have antitumor activity. The activity against ascitic tumors, including P388/O, is evidenced by reduction of tumor cell number in mammals (for example, mice bearing ascitic tumors) and their consequent increase in survival duration as compared to an untreated tumor bearing control group. Antitumor activity is further evidenced by measurable reduction in the size of solid tumors following treatment of mammals with the compounds of this invention compared to the tumors of untreated control tumor bearing animals. Compounds of formula (I) are active against murine tumors such as lymphocytic leukemia P388/O, lymphocytic leukemia L1210, melanotic melanoma B16, P815 mastocytoma, MDAY/D2 fibrosarcoma, colon 38 adenocarcinoma, M5076 rhabdomyosarcoma and Lewis lung carcinoma.

Activity in one or more of these tumor tests has been reported to be indicative of antitumor activity in man (A. Goldin et al. in *Methods in Cancer Research* ed. V. T. DeVita Jr. and H. Busch, 16 165, Academic Press, N.Y. 1979).

There are sublines of P388/O which have been made resistant to the following clinically useful agents: cytosine arabinoside, doxorubicin, cyclophosphamide, L-phenylalanine mustard, methotrexate, 5-fluorouracil, actinomycin D, cis-platin and bis-chloroethylnitrosourea. Compounds of this invention show potent activity against these drug-resistant tumors using the procedure for P388/O above.

Compounds of formula (I) have also been found to be active against human tumor cells in primary cultures of lung, ovary, breast, renal, melanoma, unknown primary, gastric, pancreatic, mesothelioma, myeloma, and colon cancer. (As used herein "cancer" is to be taken as synonymous with "malignant tumor" or more generally "tumor" unless otherwise noted.) This is a procedure in which the prevention of tumor cell colony formation, i.e. tumor cell replication, by a drug has been shown to correlate with clinical antitumor activity in man (D. D. Von Hoff et al., *Cancer Chemotherapy and Pharmacology* 6, 265 (1980); S. Salmon and D. D. Von Hoff, *Seminars in Oncology*, 8, 377 (1981)).

Compounds of formula I which have been found to have antitumor activity intercalate in vitro with DNA (this property is determined by viscometric methods using the procedure of W. D. Wilson et al., *Nucleic Acids Research* 4, 2697 (1954)) and a log P as calculated by the method of C. Hansch and A. Leo in *Substituent Constants for Correlation Analysis in Chemistry and Biology*, John Wiley and Sons, New York, 1979, lying in the range between $-2.0$ and $+2.5$.

As has been described above, the compounds of the present invention are useful for the treatment of animals (including humans) bearing susceptible tumors. The invention thus further provides a method for the treatment of tumors in animals, including mammals, especially humans, which comprises the administration of a clinically useful amount of compound of formula (I) in a pharmaceutically useful form, once or several times a day or other appropriate schedule, orally, rectally, parenterally, or applied topically.

In addition, there is provided as a further, or alternative, aspect of the invention, a compound of formula (I) for use in therapy, for example as an antitumour agent.

The amount of compound of formula (I) required to be effective as a biocidal agent will, of course, vary and is ultimately at the discretion of the medical or veterinary practitioner. The factors to be considered include the condition being treated, the route of administration, and nature of the formulation, the mammal's body weight, surface area, age and general condition, and the particular compound to be administered. a suitable effective antitumor dose is in the range of about 0.1 to about 120 mg/kg body weight, preferably in the range of about 1.5 to 50 mg/kg, for example 10 to 30 mg/kg. The total daily dose may be given as a single dose, multiple doses, e.g., two to six times per day or by intravenous infusion for selected duration. For example, for a 75 kg mammal, the dose range would be about 8 to 9000 mg per day, and a typical dose would be about 2000 mg per day. If discrete multiple doses are indicated, treatment might typically be 500 mg of a compound of formula I given 4 times per day in a pharmaceutically useful formulation.

While it is possible for the active compound (defined herein as compound of formula (I), or ether, ester, or salt thereof) to be administered alone, it is preferable to present the active compound in a pharmaceutical formulation. Formulations of the present invention, for medical use, comprise an active compound together with one or more pharmaceutically acceptable carriers thereof and optionally other therapeutical ingredients. The carrier(s) must be pharmaceutically acceptable in the sense of being compatible with the other ingredients of the formulation and not deleterious to the recipient thereof.

The present invention, therefore, further provides a pharmaceutical formulation comprising a compound of formula (I) (in the form of the free base, ether, or ester derivative or a pharmaceutically acceptable acid addition salt thereof) together with a pharmaceutically acceptable carrier therefore.

There is also provided a method for the preparation of a pharmaceutical formulation comprising bringing into association a compound of formula (I) an ether, ester, or pharmaceutically acceptable salt thereof, and a pharmaceutically acceptable carrier therefore.

While the antitumor activity of the compounds of formula (I) is believed to reside in the free base, it is often convenient to administer an acid addition salt of a compound of formula (I).

The formulations include those suitable for oral, rectal or parenteral (including subcutaneous, intramuscular and intravenous) administration. Preferred are those suitable for oral or parenteral administration.

The formulations may conveniently be presened in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Molded tablets may be made by molding in a suitable machine, a mixture of the powdered active compound with any suitable carrier.

A syrup may be made by adding the active compound to a concentrated, aqueous solution of a sugar, for example sucrose, to which may also be added any accessory ingredients. Such accessory ingredient(s) may include flavorings, an agent to retard crystallization of the sugar or an agent to increase the solubility of any other ingredient, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of the formula (I) that is isotonic with the blood of the recipient. Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isethionate and methanesulfonate salts, preferably the latter.

Useful formulations also comprise concentrated solutions or solids containing the compound of formula (I) which upon dilution with an appropriate solvent give a solution suitable for parenteral administration as above.

In addition to the aforementioned ingredients, the formulations of this invention may further include one or more accessory ingredient(s) selected from diluents, buffers, flavoring agents, binders, surface active agents, thickeners, lubricants, preservatives (including antioxidants) and the like.

The followng examples are provided by the way of illustration of the present invention and should in no way be construed as a limitation thereof.

General Comments

All solvents were reagent grade and used without further purification with the following exceptions. THF was dried by distillation from Na/K alloy under nitrogen ($N_2$) and used immediately. Toluene ($PhCH_3$) was distilled from $CaH_2$ under $N_2$ and stored over 3 Å molecular sieves. Chemicals used were reagent grade and used without purification unless noted. The full name and address of the suppliers of the reagents and chemicals is given when first cited. After this, an abbreviated name is used.

Preparative HPLC was carried out on a Water's Prep LC/System 500A machine using two 500 g silica gel ($SiO_2$) cartridges unless otherwise noted. Plugs of $SiO_2$ used for purifications were "flash chromatography" silica gel (Merck & Co., Inc., Merck Chemical Division, Rahway, NJ, 07065 silica gel 60, 230-400 mesh). In this procedure, an appropriate volume sintered glass funnel was filled approximately ¾ full with the $SiO_2$ and packed evenly by tapping the outside of the funnel. A piece of filter paper was then placed on top of the $SiO_2$ and a solution of the material to be purified applied evenly to the top. Gentle suction through a filter flask moved the eluting solvent through the plug rapidly. The appropriate size fractions were combined as needed and further manipulated.

General procedures are described in detail. Analogous procedures show melting point (mp), recrystallization solvents, and elemental analyses (all elements analyzing within a difference of $\leq 0.4\%$ of the expected value). Any changes to the procedure such as solvent, reaction temperature, reaction time, or workup are noted.

NMR ($^1H$, $^{13}C$), IR, MS data of all new products were consistent with the expected and proposed structures. The positions assigned to structural isomers were unequivocally determined by a number of NMR techniques. All final products were dried in a vacuum oven at 20 mm Hg pressure at the temperature indicated ovenight (12-16 h). All temperatures are in degrees Celsius. Other abbreviations that were used: room temperature (RT), absolute (abs.), round bottom flask (RB flask), minutes (min), hours (h).

EXAMPLE 1

2-Methyl-2-((3-perylenylmethyl)amino)-1,3-propanediol hydrochloride 1A. 3-Perylenecarbaldehyde A 3 L 3-neck flask fitted with overhead mechanical stirrer, thermometer, condenser, and $N_2$ line was charged with perylene (Aldrich Chemical Co., Milwaukee, WI, 53201, 25 g, 99 mmol) and o-dichlorobenzene (500 mL). The liquid was warmed until all the large chunks of solid dissolved (80°) and then cooled quickly to give finely divided crystals. After further cooling with a salt-ice bath to 5°, $SnCl_4$ (Aldrich, 98%, 51.2 g, 0.897 mol, 23 mL), was added in one portion. No temperature change occurred. The pot temperature was kept below 5°, and 1,1-dichloromethylmethylether (Aldrich, 14.9 g, 0.13 mol, 11.7 mL) was added dropwise over 1 h. The resulting suspension was warmed slowly to 40° over 2 h and further stirred for 16 h. Considerable HCl gas evolution occurred during the warming and the early part of the reaction at 40°. The reaction mixture was then cooled to 10° and hydrolysed by careful addition of 1 L of cold $H_2O$. After 4 h the layers were separated and the organic layer filtered, dried with anhydrous $Na_2SO_4$ (Mallinckrodt Co., 2nd and Mallinckrodt St., St. Louis, MO, 63147, 100 g) and filtered again. The clear yellow solution was passed through a 500 g plug of $SiO_2$ using $PhCH_3$ as the eluting solvent with 500 mL fractions. This chromatography separated unreacted perylene from the aldehyde and a more polar product. Fractions (5 L) containing the aldehyde were combined and the $PhCH_3$ removed. The resulting oily solid was shaken with $CH_3OH$ (200 mL) and the orange-brown crystals which formed were collected by filtration to give after drying 23.2 g (83%) of 3-perylenecarbaldehyde mp 223°-233°, (C,H), (lit. mp 236° (darkens >230°), N. P. Buu-Hoi and C. T. Long, Recueil 75 1121 (1956).

1B. 2-Methyl-2-((3-perylenylmethyl)amino-1,3-propanediol hydrochloride

To a 1 L Erlenmeyer flask was added 3-perylenecarbaldehyde (1A, 14.01 g, 50 mmol), 2-methyl-2-amino-1,3-propanediol (Aldrich, 5.52 g, 52.5 mmol), p-toluenesulfonic acid.$H_2O$ (Eastman Kodak Co., Rochester, NY, 14650, 0.1 g, 0.5 mmol), and $PhCH_3$ (300 mL). The mixture was warmed to reflux for a few minutes and $H_2O$ (2-3 mL) was driven off. The resulting orange-brown colored solution was allowed to cool to RT, diluted with absolute EtOH (300 mL) and stirred overnight. $NaBH_3CN$ (Aldrich, 95%, 1.57 g, 25 mmol) was added to the reaction. After the $NaBH_3CN$ dissolved, an indicator (bromocresol green, Eastman, 5 mg) was added. To the resulting dark blue solution was added 5 drops of 1M solution of HCl gas in absolute EtOH every 15 minutes. After 3 days the indicator turned dark green then orange and voluminous brown precipitate was present in the flask. To the flask was then added HCl gas (10 mL) in absolute EtOH. The reaction was diluted to 4 L with $Et_2O$ and stirred for 1 h. The precipitate was then collected by filtration through a medium porosity glass fritted funnel and pressed dry. The dark brown filter cake was washed thoroughly with 20% HCl (2×250 mL), pressed dry and then washed with $CH_2Cl_2$ (2×500 mL), pressed and sucked dry. The solid was recrystallized 3x from $CH_3OH/Et_2O$. After filtration, drying at 50°, 6.36 g (31%) of 2-methyl-2-((3-perylenylmethyl)amino)-1,3-propanediol hydrochloride mp 231°-232° (dec), (C,H,Cl,N).

1C.
2-Methyl-2-((3-perylenylmethyl)amino-1,3-propanediol methanesulfonate

To a 1 L RB flask equipped with magnetic stirring bar, condenser, Dean-Stark trap and $N_2$ bubbler was added perylene-3-carbaldehyde (1A, 10.0 g, 35.67 mmol), 2-amino-2-methyl-1,3-propanediol (Aldrich, 7.36 g, 70 mmol), p-toluenesulfonic acid (Aldrich, 0.1 g) and $PhCH_3$ (500 mL). The dark brown mixture was refluxed for 2 h with azeotropic removal of $H_2O$. Most of $PhCH_3$ was then distilled from the mixture (except 100 mL). This was cooled and diluted to 300 mL with abs. EtOH. $NaBH_4$ (MCB, 2.64 g, 70 mmol) was then added to the flask. The solid in the flask dissolved partially and was further diluted with $PhCH_3$ (200 mL). The mixture was then stirred at RT for 3 h. $H_2O$ (10 mL) was then added to the flask.

Solvent was then removed from the mixture by rotary evaporation to give a dark brown solid. This was shaken with $H_2O$ (500 mL) several times and finally filtered. The crude solid was disolved in a mixture of $PhCH_3$ and abs. EtOH (1:1, 200 mL) and treated with $CH_3SO_3H$ (Aldrich, 3 mL). The solution was then filtered and diluted with $Et_2O$ to give 8.08 g (48.7%) of 2-methyl-2-((3-perylenylmethyl)amino-1,3-propanediol methanesulfonate mp 211°-213° (dec), (C,H,N,S). In some of the analogous procedures following, ethanolic HCl was used instead of methanesulfonic acid to give the corresponding hydrochloride salt.

EXAMPLE 2
(+ −)(2R*,3S*)-2-((3-Perylenylmethyl)amino)-2-methyl-1,3-butanediol 2A. (+ −)(2R*,3R*)-2-Methyl-2-nitro-1,3-butanediol and 2B. (+ −)(2R*,3R*-2-Methyl-2-nitro-1,3-butanediol To a mixture of 2-nitro-1-propanol (Aldrich, 63.0 g, 0.60 mol) and acetaldehyde (Eastman, 39.6 g, 0.90 mol) cooled in an ice bath under $N_2$ was added cold $H_2O$ (40 mL) and calcium hydroxide (200 mg). The mixture was allowed to warm to RT over 2 h and then stirred for 68 h. The resulting solution was neutralized with excess solid $CO_2$. The mixture was stirred for 1 h before filtration through a Millipore ® filter (Millipore Corp., Bedford, MA, 01730). The filtrate was then concentrated under vacuum at 35°. The residue, a viscous syrup which partially crystallized on drying under vacuum (0.1 mm, RT, 48 h), was triturated with cold $Et_2O$ (35 mL). Solid white crystals which formed were collected by filtration, washed with cold $Et_2O$ (3×15 mL) and dried under vacuum (0.1 mm, RT) to give 34.1 g of material, judged by NMR to be (+ −)(2R*,3S*)-2-methyl-2-nitro-1,3-butanediol (2A) (purity >97%, racemic). After recrystallization, the diastereomeric purity was >99%, mp 78.5°-81° (lit. 78°; cf. Beil 1, 482 in Henry, Bull. Soc. Chim. Fr. [3] 15, 1224), (C,H,N).

The original filtrate (including washes) was concentrated under vacuum to a pale yellow liquid which was subjected to flash chromatography as follows: The sample was mixed with hexane:EtOAc (2:1, 100 mL) and added to a column of dry $SiO_2$ (1.5 kg). The column was eluted with hexane:EtOAc (2:1, 12 L) then hexane:EtOAc (1:1, 6 L) while 500 mL fractions were collected. Appropriate fractions were combined. Pure product was found in the final 8 L; yield, 38.7 g of viscous syrup, judged by NMR to be a 1:1 mixture of the two racemic diastereomers (2A and 2B), (C,H,N).

This and another batch of the 1:1 diastereomeric mixture of 2A and 2B (prepared as described above) were combined (67 g, total) and subjected to successive liquid-liquid partitioning between $H_2O$ and EtOAc to give pure samples (99% on the basis of NMR and HPLC (Hamilton PRP-1 column using 3.5% aqueous acetonitrile as the mobile phase)) of (+ −)(2R*,3S*)-2-methyl-2-nitro-1,3-butanediol (2A) (24.9 g, k′=4.3, C,H,N) and (+ −)(2R*,3S*)-2-methyl-2-nitro-1,3-butanediol (2B) (15.8 g, k′=2.1, C,H,N, a colorless, viscous liquid).

2C.
(+ −)(2R*,4S*,5R*)-4,5-dimethyl-5-nitro-2-phenyl-1,3-dioxane and

2D.
(+ −)(2R*,4S*,5S*)-4,5-dimethyl-5-nitro-2-phenyl-1,3-dioxane

The relative configurations of these two diastereomeric pairs (2A and 2B) were unequivocably assigned on the basis of comparative NMR analysis of the respective cyclic acetals derived from benzaldehyde. Thus, 2A (1.49 g, 0.01 mol) and benzaldehyde (Mallinckrodt, 1.06 g, 0.01 mol) were condensed in benzene in the presence of a catalytic amount of p-toluenesulfonic acid with azeotropic removal of water (according to the method of H. Piotrowska, B. Serafin and T. Urbanski, Tetrahedron 109, 379 (1963)). After successive washing with satd. $NaHCO_3$ solution, drying ($MgSO_4$), filtration, and removal of the benzene by rotary evaporation, a pale yellow solid was obtained. A solution of this product in ethanol at 0° C. provided an oil which was isolated by decanting the mother liquor and drying under vacuum (0.1 mm, RT). The yield was 1.48 g (62%) of (+ −)(2R*,4S*,5R*)-4,5-dimethyl-5-nitro-2-phenyl-1,3-dioxane (2C) (C,H,N).

Similarly prepared from 2B and benzaldehyde was (+ −)(2R*,4S*,5S*)-4,5-dimethyl-5-nitro-2-phenyl-1,3-dioxane (2D) (74%) (C,H,N).

2E. (+ −)(2R*,3R*)-2-Amino-2-methyl-1,3-butanediol acetate

To a solution of (+ −)(2R*,3R*)-2-methyl-2-nitro-1,3-butanediol (2B, 22.1 g, 0.148 mol) in 95% EtOH (150 mL) was added glacial acetic acid (25 mL) and 10% Pd/C (MCB, 2.0 g). The reduction was carried out in a Parr apparatus at 50 psi of $H_2$ during a 48 h period at RT. The catalyst was removed by filtration through a Millipore ® filter, and the solvent removed under vacuum (2 days). The viscous, colorless syrup was dissolved in abs. EtOH (30 mL). Dilution with abs. $Et_2O$ (300 mL) gave a cloudy liquid which was placed in a refrigerator for two days. During this time, colorless crystals formed. They were washed with $Et_2O$ and dried in a vacuum oven at RT for two days. The yield of (+ −)(2R*,3R*)-2-amino-2-methyl-1,3-butanediol acetate was 25.6 g (97%) mp 117°-121°, (C,H,N).

2F. (+ −)(2R*,3S*)-2-Amino-2-methyl-1,3-butanediol acetate

Using the reduction procedure in 2E, (+ −)(2R*,3S*)-2-methyl-2-nitro-1,3-butanediol (2A)

gave (+−)(2R*,3S*)-2-amino-2-methyl-1,3-butanediol acetate (93%) (C,H,N) mp 163°–165° C.

2G.
(+−)(2R*,3S*)-2-((3-Perylenylmethyl)amino)-2-methyl-1,3-butanediol methanesulfonate 2/10 H<sub>2</sub>O To a RB flask was added (+−)(2R*,3S*)-2-amino-2-methyl-1,3-butanediol acetate (2F) and an equimolar amount of NaOCH<sub>3</sub> and CH<sub>3</sub>OH (100 mL). After warming, the solvent was removed by rotary evaporation, and after addition of perylene-3-carbaldehyde, the reaction run following the reductive amination procedure outlined in 1C to give (+−)(2R*,3S*)-2-((3-perylenylmethyl)amino)-2-methyl-1,3-butanediol methanesulfonate. 2/10 H<sub>2</sub>O mp 193.5°–194.5° (dec), (C,H,N,S).

EXAMPLE 3

2-((3-Perylenylmethyl)amino)-2-ethoxymethyl-1,3-propanediol 3A.
3,5-Diphenyl-7a(7H)-ethoxymethyl-1H,3H,5H-oxazolo(3,4-c)oxazole A mechanically stirred 60% dispersion of NaH in mineral oil (Morton Thiokol, Inc.—Alfa Products, P.O. Box 299, 152 Andover Street, Danvers, MA, 01923, 34.0 g, 0.85 mol) was washed with dry hexane to remove the oil and suspended in dry DMF (300 mL). To the mixture was added a solution of 3,5-diphenyl-1H,3H,5H-oxazolo(3,4-c)oxazole-7a(7H)-methanol 208.2 g, 0.7 mol, prepared by the method of J. Pierce et al., *J. Amer. Chem. Soc.* 73 2595 (1951)) in dry DMF (300 mL) keeping the reaction mixture between 30°–35°. The salt suspension was stirred at RT for 60 min, diluted with dry DMF (200 mL) to facilitate stirring, cooled, then treated with ethyl iodide (Aldrich, excess) at such a rate that the reaction temperature was between 20°–35°. The mixture was stirred at RT for 2 h, then cautiously treated with abs. EtOH (30 mL). The resulting mixture was diluted with Et<sub>2</sub>O (2.5 L) and the resulting solids removed by filtration. The solvent was then removed using a rotary evaporator to give 229.5 g of a yellow oil containing both starting material and desired product. A solution of the oil in chloroform was mixed with SiO<sub>2</sub> (200 g) and the solvent removed. The solid was then added to a column of SiO<sub>2</sub> (800 g). Elution with the EtOAc/hexane (1:3.5) gave 139.7 g (61.3%) of 3,5-diphenyl-7a(7H)-ethoxymethyl-1H,3H,5H-oxazolo(3,4-c)oxazole. An analytical sample was obtained by recrystallization from hexane, mp 83.5°–85.0°, (C,H,N). The bulk of the material was used without further purification.

3B. 2-Amino-2-ethoxymethyl-1,3-propanediol hydrochloride ¼H<sub>2</sub>O 3,5-Diphenyl-7a(7H)-ethoxymethyl-1H,3H,5H-oxazolo(3,4-c)oxazole (3A, 136 g, 0.42 mol) was dissolved in 6N HCl (400 mL) and the resulting solution stirred 1.5 h at RT. After extraction with Et<sub>2</sub>O (2×200 mL) to remove benzaldehyde, the aqueous solution was concentrated on a rotary evaporator to give a colorless oil. This was cooled in an ice bath to facilitate crystallization. The solid which formed was slurried with cold CH<sub>3</sub>CN, filtered, then washed with Et<sub>2</sub>O and dried in a vacuum oven at RT to give 71 g (89%) of 2-amino-2-ethoxymethyl-1,3-propanediol hydrochloride.¼H<sub>2</sub>O mp 78°–79°, (C,H,Cl,N).

3C.
2-((3-Perylenylmethyl)amino-2-ethoxymethyl-1,3-propanediol methanesulfonate ¾H<sub>2</sub>O To a RB flask was added 2-amino-2-ethoxymethyl-1,3-propanediol hydrochloride.¼H<sub>2</sub>O (3B) and an equimolar amount of NaOCH<sub>3</sub> and CH<sub>3</sub>OH (100 mL). After warming, the solvent was removed by rotary evaporation, and after addition of perylene-3-carbaldehyde (1A) the reaction run following the reductive examination procedure outlined in 1C to give 2-((3-perylenylmethyl)amino)-2-ethoxymethyl-1,3-propanediol methanesulfonate.¾H<sub>2</sub>O mp 188°–190° (dec), (EtOH/Et<sub>2</sub>O), (C,H,N,S).

EXAMPLE 4

2-((3-Perylenylmethyl)amino)-3-methoxy-2-methyl-1-propanol 4A.
4-Aza-3-hydroxymethyl-3-methyl-1-oxaspiro[4.5]decane A solution of 2-amino-2-methyl-1,3-propanediol (Aldrich, 303.4 g, 3.0 mol), cyclohexanone (Aldrich, 294.5 g, 3.0 mol) and PhCH<sub>3</sub> (400 mL) was refluxed for approximately 2 h with azeotropic removal of H<sub>2</sub>O. The material which crystallized from the PhCH<sub>3</sub> on cooling was recrystallized twice from hexane to give 444.4 g of 4-aza-3-hydroxymethyl-3-methyl-1-oxaspiro[4.5]decane (80%) mp 52°–54°, (C,H,N).

4B.
4-Aza-3-methoxymethyl-3-methyl-1-oxaspiro[4.5]decane

A mechanically stirred 60% dispersion of NaH in mineral oil (Alfa, 75 g, 1.9 mol) was washed with dry hexane to remove the oil and suspended in dry DMF (200 mL). To the mixture was added a solution of 4-aza-3-hydroxymethyl-3-methyl-1-oxaspiro[4.5]decane (4A, 27.8 g, 1.5 mol) in dry DMF (200 mL) keeping the reaction mixture temperature between 30°–35°. Small amounts of DMF were added as necessary to facilitate stirring. The mixture was stirred at RT for 1.5 h, then cooled and treated with methyl iodide (Fisher, 234.2 g, 102.7 mL, 1.65 mol) keeping the reaction temperature between 20°–30°. The mixture was stirred 2 h at RT and slowly treated with absolute EtOH (40 mL), then diluted with dry Et<sub>2</sub>O (3 L). The reaction mixture was filtered and the solvent removed by rotary evaporation. The residue was then fractionally distilled to give 209.7 g (70.3%) of 4-aza-3-methoxymethyl-3-methyl-1-oxaspiro[4.5]decane as a colorless liquid bp 114°/14 mm, (C,H,N).

4C. 2-Amino-3-methoxy-2-methyl-1-propanol

A solution of 4-aza-3-methoxymethyl-3-methyl-1-oxaspiro(4.5)decane (299 g, 1.5 mol) and 6N HCl (500 mL) was refluxed for 60 min. On cooling, two layers formed, the upper one containing cyclohexanone was removed by extraction with Et<sub>2</sub>O (2×400 mL). The lower aqueous layer was concentrated on a rotary evaporator to give a syrup which then was treated with excess 50% NaOH. The resulting slurry was extracted with Et<sub>2</sub>O/CH<sub>2</sub>Cl<sub>2</sub> (2:1, 4×500 mL), then with CH<sub>2</sub>Cl<sub>2</sub> (500 mL). The solvent was removed by rotary evaporation to give 198 g of pale oil. Fractional distillation of this oil gave 166 g (93%) of 2-amino-3-methoxymethyl-1-propanol as a colorless oil, bp 94° C./17 mm, (C,H,N).

4D. 2-((3-Perylenylmethyl)amino)-3-methoxy-2-methyl-1-propanol methanesulfonate ¼H₂O 3/10 EtOH Using the reductive amination procedure outlined in 1C, perylene-3-carbaldehyde (1A) and 2-amino-3-methoxy-2-methyl-1-propanol (4C) gave 2-((3-perylenylmethyl)amino)-3-methoxy-2-methyl-1-propanol methanesulfonate.¼H₂O.3/10EtOH mp 194°–197° (dec), (EtOH/Et₂O), (C,H,N,S).

EXAMPLE 5

2-Methyl-2-((3-Perylenylmethyl)amino)-1,4-butanediol

5A. Ethyl N-benzylidene-1-alaninate

Ethyl N-benzylidene-1-alaninate was prepared according to the general procedure of G. Stork et al., *J. Org. Chem.* 41, 349 (1976), bp 98°–100°/0.4 mm (lit. 100°/0.3 mm, A. Calcagni et al., Synthesis 445 (1981)).

5B. 2-(2-Iodoethoxy)tetrahydro-2-H-pyran

Freshly distilled dihydropyran (Aldrich, 59.0 g, 0.7 mol) was added dropwise to a cooled solution of iodoethanol (Aldrich, 98 g, 0.57 mol) in Et₂O (1 L) containing 0.1 g of p-toluenesulfonic acid (Eastman). The solution was then stirred for 1 h at 5°. Solid K₂CO₃ (Mallinckrodt, 5 g) was then added to the reaction mixture and the resulting suspension stirred an additional 1 h at RT. The reaction was then filtered and the remaining solid washed with Et₂O (1L). The organic solutions were combined and concentrated on a rotary evaporator (in a flask washed with 1% NEt₃ in H₂O). The crude 2-(2-iodoethoxy)-tetrahydro-2-H-pyran (100 g, 68.9%) was used without further purification.

5C. Ethyl 2-benzylideneamino-2-methyl-4-((tetrahydro-2H-pyran-2-yl)oxy)butyrate A solution of lithium diisopropylamide was prepared by dropwise addition of n-BuLi (Aldrich, 1.6M in hexane, 228 mL, 0.365 mol) to a solution of diisopropylamine (Aldrich, 51.6 g, 0.51 mol) in a mixture of dry THF (700 mL) and dry HMPA (Aldrich, 40 mL) kept at 30°–40°. The solution was then cooled to −70° and a solution of ethyl N-benzylidene-1-alaninate (5A, 74.9 g, 0.365 mol) was added dropwise to the solution allowing the reaction mixture warm to −20° for several min. The resulting red solution was then cooled to −70°. (2-Iodoethoxy)tetrahydro-2-H-pyran (5B, 98.1 g, 0.383 mol) was then added to the solution at such a rate that the temperature in the reaction mixture did not rise above −65°. The solution was allowed to warm slowly to RT and stirred for 14 h. The volume of the solution was reduced to 300 mL by a stream of dry N₂ during the last few hours to facilitate the final workup. The reaction was quenched with sat. NaCl (800 mL) and diluted with Et₂O (800 mL). The Et₂O was removed and the aqueous layer extracted with hexane (500 mL). The Et₂O and hexane layers were combined and dried (Na₂SO₄). The solution was filtered and the solvent removed to give 124 g of crude red oil. Bulb to bulb distillation (in 1% aq. NEt₃ washed glassware) (210° bath temperature/0.3 mm) gave 95 g of ethyl 2-benzylideneamino-2-methyl-4-((tetrahydro-2H-pyran-2-yl)oxy)butyrate which was homogeneous by vpc and gave acceptable NMR and mass spectra. It was stored under N₂ in the refrigerator and was used without further purification.

5D. 2-Benzylamino-2-methyl-4-((tetrahydropyran-2-yl)oxy)butanol

A solution of ethyl 2-benzylideneamino-2-methyl-4-((tetrahydro-2H-pyran-2-yl)oxy)butyrate (5C, 100.0 g, 0.3 mol) in THF (100 mL) was added slowly to a suspension of lithium aluminum hydride (Alfa, 22.77 g, 0.6 mol) rapidly stirred in dry THF (1 L) at such a rate to maintain a gentle reflux. After the addition was complete the mixture was refluxed for 4 h. The reaction mixture was cooled and treated successively with H₂O (23 mL), 15N NaOH (23 mL) and H₂O (45 mL). The solid was removed by filtration and washed with THF (200 mL). The organic layers were combined and concentrated by rotary evaporation to give 2-benzylamino-2-methyl-4-((tetrahydropyran-2-yl)oxy)butanol (81.1 g, 92.0%) as a thick oil which was used without further purification.

5E. 2-Benzylamino-2-methyl-1,4-butanediol

The crude 2-benzylamino-2-methyl-4-((tetrahydropyran-2-yl)oxy)butanol (5D, 80.1 g, 0.273 mol) was dissolved in 3N HCl (128 mL). After 5 min the mixture was washed with Et₂O (200 mL). The aqueous solution was concentrated by rotary evaporation to give a thick oil which was cooled and basified with excess 50% NaOH. The oily amine which formed was extracted with Et₂O (3×200 mL). The Et₂O extracts were combined and concentrated to give 63.6 g of a thick oil. Distillation gave 49.8 g (94%) of 2-benzylamino-2-methyl-1,4-butanediol as a pale yellow oil (bp 168°–170°/0.35 mm) (C,H,N).

5F. 2-Amino-2-methyl-1,4-butanediol hydrochloride

2-Benzylamino-2-methyl-1,4-butanediol (5E, 31.08 g, 0.149 mol) was dissolved in 95% EtOH (240 mL) containing concentrated HCl (21 mL, 0.25 mol) and 5% Pd/C (10.0 g) and reduced in a Parr apparatus at 40 psi over 37 h at RT. The catalyst was then removed by filtration and the solvent removed by rotary evaporation (bath at 60°) to give 20.91 g of 2-amino-2-methyl-1,4-butanediol hydrochloride (90.2%) as a clear, thick, colorless oil with acceptable NMR and mass spectra. It was used without further purification. This compound has been reported as its acetate salt (G. Cardillo et al., *Chem. Commun.* 1308, 1982), but no data was given. Attempts to duplicate the latter procedure were unsuccessful.

5G. 2-Methyl-2-((3-perylenylmethyl)amino)-1,4-butanediol methanesulfonate-3/10 H₂O To a RB flask was added 2-amino-2-methyl-1,4-butanediol hydrochloride (5F) and an equimolar amount of NaOCH₃ and CH₃OH (100 mL). After warming, the solvent was removed by rotary evaporation, and after addition of perylene-3-carbaldehyde, the reaction run following the reductive amination procedure outlined in 1C to give 2-methyl-2-((3-perylenylmethyl)amino)-1,4-butanediol methanesulfonate.3/10 yH₂O mp 182°–184° (dec), (EtOH/Et₂O), (C,H,N,S).

EXAMPLE 6

(1α,2β,3α)-2-(3-Perylenylmethyl)amino)-1,3-cyclohexamediol

6A. (1α,2β,3α)-2-Amino-1,3-cyclohexanediol acetate

This compound was prepared by the method of F. Lichtenthaler (Ber. 96, 851 (1963), mp 175°–177°, (C,H,N), (lit. 178°–179°, F. Lichtenthaler, Ber. 96, 845 (1963).

6B. (1α,2β,3α)-2-((3-Perylenylmethyl)amino)-1,3-cyclohexanediol methanesulfonate Using the reductive amination procedure outlined for 2G, perylene-3-carbaldehyde (1A) and (1α,2β,3α)-2-amino-1,3-cyclohexanediol acetate (6A) gave (1α,2β,3α)-2-((3-perylenylmethyl)amino)-1,3-cyclohexanediol methanesulfonate mp 237°–240° (dec), (CH₃OH/Et₂O), (C,H,N,S).

EXAMPLE 7

2-Isopropyl-2-((3-perylenylmethyl)amino)-1,3-propanediol

7A. 2-Isopropyl-2-nitro-1,3-propanediol

A solution of 2-methyl-1-nitropropane (38.7 g, 0.375 mol prepared by the procedure of N. Kornblum, B. Taube, and H. Ungnade, *J. Am. Chem. Soc.* 76, 3209 (1954) and NEt₃ (Eastman 3.79 g, 0.0375 mol) in CH₃OH (50 mL) was added dropwise 37% aqueous formaldehyde solution (Mallinckrodt, 76.2 g, 0.938 mol), at a rate such that the reaction mixture temperature did not exceed 30°. After 72 h, the solution was concentrated under vacuum and the residue was dissolved in H₂O (250 mL). The solution was continuously extracted for 1 h with CH₂Cl₂ (1 L). The CH₂Cl₂ solution was dried (MgSO₄), filtered, and concentrated to give 53.3 g (87%) of 2-isopropyl-2-nitro-1,3-propanediol a waxy, white solid mp 67°–72° (lit. mp 87°–88°, B. M. Vanderbilt and H. B. Hass, *Ind. Eng. Chem.* 32, 34 (1940). In our hands this procedure failed to give the desired compound).

7B. 2-Amino-2-isopropyl-1,3-propanediol acetate

Using the procedure in 2E, 2-isopropyl-2-nitro-1,3-propanediol gave a 98% yield of 2-amino-2-isopropyl-1,3-propanediol acetate mp 155°–155.5°. H. S. Broadbent et al., *J. Heterocyclic Chem.*, 13, 337 (1975) report the synthesis of this compound as the free base (mp 70°–72°)).

7C. 2-Isopropyl-2-((3-perylenylmethyl)amino)-1,3-propanediol methanesulfonate ½H₂O To a RB fask was added 2-amino-2-isopropyl-1,3-propanediol acetate.½H₂O (7B) and an equimolar amount of NaOCH₃ (MCB) and CH₃OH (100 mL). After warming, the solvent was removed by rotary evaporation and after addition of perylene-3-carbaldehyde (1A), the reaction run following the normal reductive amination procedure outlined in 1C to give 2-isopropyl-2-((3-perylenylmethyl)amino)-1,3-propanediol methanesulfonate.½H₂O mp 189°–191° (dec), (EtOH/Et₂O), (C,H,N,S).

Antitumor Screening Results

Methods for evaluating the antitumor activity of these compounds are essentially those used in the Tumor Panel by the Developmental Therapeutics Program, Division of Cancer Treatment, National Cancer Institute, A. Goldin, et al., *Methods in Cancer Research*, Vol. XVI, p. 165, Academic Press (1979). Some modifications in dose level and schedule have been made to increase the testing efficiency.

EXAMPLE 8

Lymphocytic Leukemia P388/0 Test

CD2-F₁ mice, of the same sex, weighing 20±3 g, are used for this test. Control and test animals are injected intraperitoneally with a suspension of ~10⁶ viable P388/0 tumor cells on day 0. In each test, several dose levels which bracket the LD₂₀ of the compound are evaluated; each dose level group contains 6 animals. The test compounds are prepared either in physiologic saline containing 0.05% Tween 80 or distilled water containing 5% dextrose and are administered intraperitoneally on days 1, 5, and 9 relative to tumor implant. Doses are on a mg/kg basis according to individual animals' body weights. The day of death for each animal is recorded, the median identified for each group and the ratios of median survival time for treated (T)/control (C) groups are calculated. The criterion for activity is T/C×100≧120%. Results of P388/0 testing are summarized in Table I below.

TABLE I

P388/0 SCREENING RESULTS

| Compound of Example No. | Optimal Dose (mg/kg) | T/C × 100% (Excluding 30 Day Survivors) | LD$_{20}^{a}$ |
|---|---|---|---|
| 1B | 262 | +209 | 175 |
| 4D | 300 | +120 | (675) |
| 2G | 200 | +205 | 325 |
| 3C | 590 | +140 | (675) |
| 7C | 110 | +120 | (675) |
| 5G | 375 | +130 | 225 |

$^{a}$Values in parentheses are the highest non-toxic dose where the LD₂₀ was not determined.

EXAMPLE 9

Melanotic Melanoma B16

B6C3-F₁ mice of the same sex, weighing 20±3 g, are used for this test. A suspension of B16 cells is prepared from a non-necrotic portion of solid tumor tissue obtained from a passage mouse. One gram of tumour is homogenized in 9 mL ice-cold Earle's salts solution and filtered through 1000 mesh screen to remove debris. 0.5 mL of the resulting brei is injected intraperitoneally into each animal. Dosing is carried out as in the P388/0 and L1210 tests. Days of death are recorded for a 60 day period, and T/C ratio calculated as in the P388/0 and L1210 tests. The criterion for activity is T/C×100≧125%. The results of B16 testing are summarized below in Table II.

TABLE II

Screening Results for B16 Melanoma

| Compound of Example No. | Dose (mg/kg) | T/C × 100% Excluding 60 day Survivors |
|---|---|---|
| 1B | 275 | +173 |

EXAMPLE 10

Formulation Examples

A. TABLET

| | |
|---|---|
| Compound of Formula I | 500.0 mg |
| Pregelatinized Corn Starch | 60.0 mg |
| Sodium Starch Glycolate | 36.0 mg |
| Magnesium Stearate | 4.0 mg |

The compound of formula (I) is finely ground and intimately mixed with the powdered excipients, pregelatinized corn starch and sodium starch glycolate. The powders are wetted with purified water to form granules. The granules are dried and mixed with the magnesium stearate. The formulation is then compressed into tablets weighing approximately 600 mg each.

B. TABLET

| | |
|---|---|
| Compound of formula (I) | 500.0 mg |
| Corn Starch | 70.0 mg |
| Lactose | 83.8 mg |
| Magnesium Stearate | 4.2 mg |
| Polyvinylpyrrolidone | 14.0 mg |
| Stearic Acid | 28.0 mg |

The compound of formula (I) is finely ground and intimately mixed with the powdered excipients, corn starch and lactose. The powders are wetted with a solution of polyvinylpyrrolidone dissolved in purified water and denatured alcohol to form granules. The granules are dried and mixed with the powdered stearic acid and magnesium stearate. The formulation is then compressed into tablets weighing approximately 700 mg each.

C. CAPSULES

| | |
|---|---|
| Compound of formula (I) | 500.0 mg |
| Corn Starch | 50.0 mg |
| Magnesium Stearate | 3.0 mg |

The finely divided compound of formula (I) is mixed with powdered corn starch and wetted with denatured alcohol to densify the powder. The dried powder is mixed with stearic acid and filled into hard-shell gelatin capsules.

D. SYRUP

| | |
|---|---|
| Compound of formula (I) | 250.0 mg |
| Ethanol | 250.0 mg |
| Glycerin | 500.0 mg |
| Sucrose | 3,500.0 mg |
| Flavoring Agent | q.s. |
| Coloring Agent | q.s. |
| Preserving Agent | 0.1% |
| Purified Water q.s. to | 5.0 mL |

The compound of formula (I) is dissolved in the ethanol, glycerin, and a portion of the purified water. The sucrose and preserving agent are dissolved in another portion of hot purified water, and then the coloring agent is added and dissolved. The two solutions are mixed and cooled before the flavoring agent is added. Purified water is added to final volume. The resulting syrup is throughly mixed.

E. IV INJECTION

| | |
|---|---|
| Compound of formula (I) | 5.0 mg |
| Glycerin | q.s. for isotonicity |
| Preservative | 0.1% |
| Hydrochloric Acid or Sodium Hydroxide | as needed for pH adjustment |
| Water for Injection | q.s. to 1 mL |

The compound of formula (I) and preservative is added to the glycerin and a portion of the water for injection. The pH is adjusted with hydrochloric acid or sodium hydroxide. Water for injection is added to final volume and solution is complete after thorough mixing. The solution is sterilized by filtration through a 0.22 micrometer membrane filter and aseptically filled into sterile 10 mL ampules or vials.

What is claimed is:

1. A compound of formula (I)

$$ArCH_2R^1 \qquad (I)$$

wherein

Ar is a perylene ring optionally substituted by one or two substituents, the substituents containing not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the perylene ring is optionally substituted by a group $NR^3R^4$ containing not more than 5 carbon atoms wherein $R^3$ and $R^4$ are the same or different and each is a $C_{1-3}$ alkyl group $R^1$ contains not more than eight carbon atoms and is a group

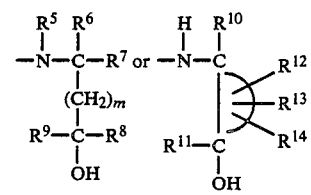

wherein m is 0 or 1;

$R^5$ is hydrogen;

$R^6$ and $R^7$ are the same or different and each is hydrogen or $C_{1-3}$ alkyl optionally substituted by hydroxy;

$R^8$ and $R^9$ are the same or different and each is hydrogen or $C_{1-3}$ alkyl;

is a five- or six-membered saturated carbocyclic ring;

$R^{10}$ is hydrogen, methyl or hydroxymethyl;

$R^{11}$, $R^{12}$ and $R^{13}$ are the same or different and each is hydrogen or methyl;

$R^{14}$ is hydrogen, methyl, hydroxy, or hydroxymethyl, and the ether, esters and acid addition salts thereof wherein said compounds of formula (I) contain no more than 30 carbon atoms.

2. A compound of claim 1 wherein Ar is 3-perylenyl,

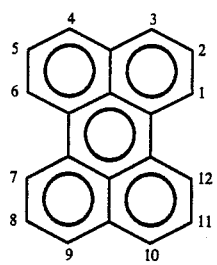

$R^1$ is

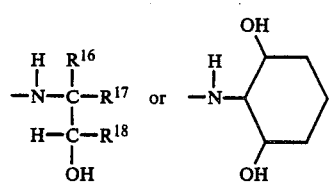

wherein
m is 0; $R^{16}$ is $CH_2OH$, $CH(CH_3)OH$ or $CH_2CH_2OH$; $R^{17}$ is hydrogen, $C_{1-3}$ alkyl or $CH_2OH$; $R^{18}$ is hydrogen or methyl; or a monomethyl or monoethyl ether thereof containing no more than 28 carbon atoms in total.

3. A compound of claim 2 wherein $R^{16}$ is $CH_2OH$ or $CH(CH_3)OH$ and $R^{17}$ is hydrogen, methyl, ethyl or $CH_2OH$.

4. A compound of claim 3 wherein $R^1$ is a diol of the structure

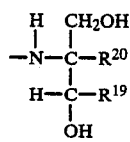

wherein $R^{19}$ is hydrogen or methyl and $R^{20}$ is hydrogen, methyl or ethyl.

5. A compound of claim 4 wherein $R^{20}$ is methyl.

6. A compound of claim 1 wherein a compound of formula I is selected from:
2-((3-Perylenylmethyl)amino)-3-methoxy-2-methyl-1-propanol,
(+−)(2R*,3S*)-2-((3-Perylenylmethyl)amino)-2-methyl-1,3-butanediol,
2-((3-Perylenylmethyl)amino)-2-ethoxymethyl-1,3-propanediol,
2-Isopropyl-2-((3-perylenylmethyl)amino)-1,3-propanediol,
2-Methyl-2-((3-perylenylmethyl)amino)-1,4-butanediol and
(1α,2β,3α)-2-((3-Perylenylmethyl)amino)-1,3-cyclohexanediol.

7. A compound of claim 6 as an acid addition salt of hydrochloric, methanesulfonic, ethanesulfonic, lactic, citric or isethionic acids.

8. A pharmaceutical formulation containing a compound of formula (I)

$$ArCH_2R^1 \qquad (I)$$

wherein
Ar is a perylene ring optionally substituted by one or two substituents, the substituents containing not more than four carbon atoms in total when taken together being the same or different and are selected from halogen; cyano; $C_{1-4}$ alkyl or $C_{1-4}$ alkoxy, each optionally substituted by hydroxy or $C_{1-2}$ alkoxy; halogen substituted $C_{1-2}$ alkyl or $C_{1-2}$ alkoxy; a group $S(O)_nR^2$ wherein n is an integer 0, 1 or 2 and $R^2$ is $C_{1-2}$ alkyl optionally substituted by hydroxy or $C_{1-2}$ alkoxy; or the perylene ring is optionally substituted by a group $NR^3R^4$ containing not more than 5 carbon atoms wherein $R^3$ and $R^4$ are the same or different and each is a $C_{1-3}$ alkyl group;
$R^1$ contains not more than eight carbon atoms and is a group

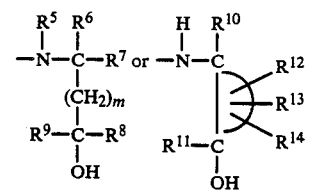

wherein
m is 0 or 1;
$R^5$ is hydrogen;
$R^6$ and $R^7$ are the same or different and each is hydrogen or $C_{1-3}$ alkyl optionally substituted by hydroxy providing that at least one hydroxy group is present;
$R^8$ and $R^9$ are the same or different and each is hydrogen or $C_{1-3}$ alkyl;

is a five- or six-membered saturated carbocyclic ring;
$R^{10}$ is hydrogen, methyl or hydroxymethyl;
$R^{11}$, $R^{12}$ and $R^{13}$ are the same or different and each is hydrogen or methyl;
$R^{14}$ is hydrogen methyl, hydroxy, or hydroxymethyl with a pharmaceutically acceptable carrier in the form of a tablet, capsule, syrup, or injection, and the ethers, esters and acid addition salts thereof wherein said compounds of formula (I) contain no more than 30 carbon atoms.

9. A pharmaceutical formulation of claim 8 wherein the compound of formula (I) is 2-methyl-2-((3-perylenylmethyl)amino)-1,3-propanediol methanesulfonate.

10. A pharmaceutical formulation of claim 8 in the form of an injection.

11. A pharmaceutical formulation of claim 9 in the form of an injection.

* * * * *